United States Patent [19]
Gill

[11] Patent Number: 6,051,004
[45] Date of Patent: Apr. 18, 2000

[54] COMBINATION NEEDLE HOLDER AND SUTURE CUTTER MEDICAL INSTRUMENT

[76] Inventor: Darrell Gill, 11900 Edgewater Dr. #1203, Lakewood, Ohio 44107

[21] Appl. No.: 09/398,857

[22] Filed: Sep. 20, 1999

[51] Int. Cl.[7] .................................................. A61B 17/04
[52] U.S. Cl. ........................ 606/147; 606/148; 606/207
[58] Field of Search ..................... 606/145–147, 606/167, 205–207

[56] References Cited

U.S. PATENT DOCUMENTS

| | | | |
|---|---|---|---|
| 2,315,326 | 3/1943 | Gmeiner | 606/147 |
| 2,998,649 | 9/1961 | Miller . | |
| 3,443,313 | 5/1969 | Profy . | |
| 4,271,838 | 6/1981 | Lasner et al. . | |
| 4,669,470 | 6/1987 | Brandfield . | |
| 4,949,717 | 8/1990 | Shaw | 606/147 |
| 5,196,023 | 3/1993 | Martin . | |
| 5,417,701 | 5/1995 | Holmes | 606/207 |
| 5,624,454 | 4/1997 | Palti et al. | 606/151 |
| 5,693,069 | 12/1997 | Shallman | 606/205 |
| 5,797,919 | 8/1998 | Brinson | 606/207 |

*Primary Examiner*—Gary Jackson
*Attorney, Agent, or Firm*—Fay, Sharpe, Fagan, Minnich & McKee, LLP

[57] ABSTRACT

A combination needle holder and suture cutter medical instrument is disclosed. The surgical instrument includes a first handle pivotally joined to a second handle to define opposing jaws at a distal end of the surgical instrument, each of the jaws including a distal clamping portion and at least one of the jaws includes a blade portion proximate a clamping portion. The blade portion includes a recessed cutting edge so as to define an aperture between the jaws in a closed position of the surgical instrument. The distal clamping portions cooperate to clamp a needle and the recessed cutting edge is adapted to independently sever a suture.

20 Claims, 3 Drawing Sheets

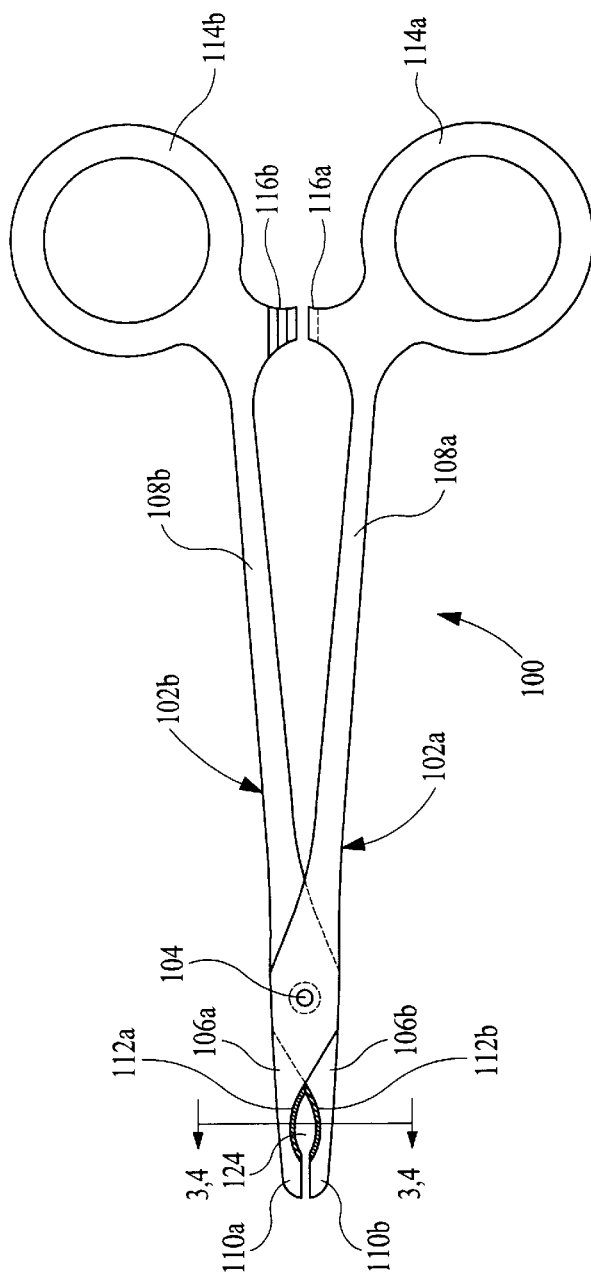
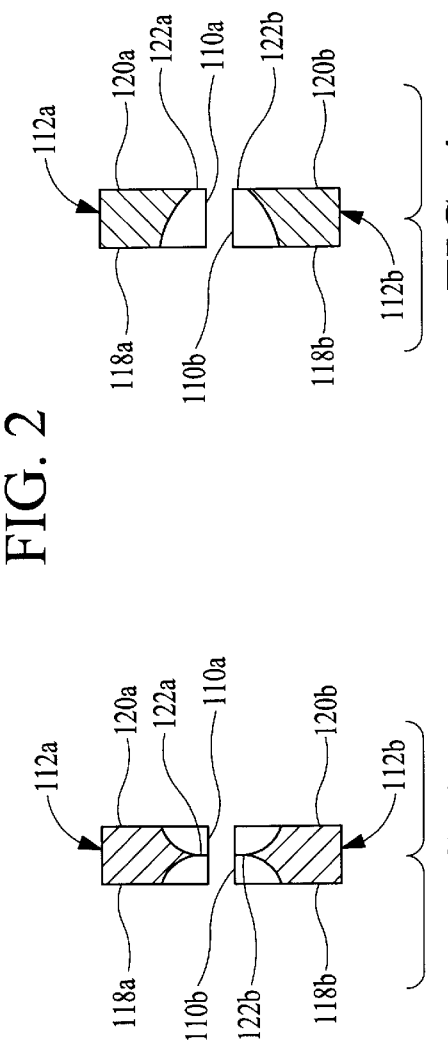
FIG. 2
FIG. 3
FIG. 4

COMBINATION NEEDLE HOLDER AND SUTURE CUTTER MEDICAL INSTRUMENT

BACKGROUND OF THE INVENTION

The present invention relates to the medical instrument arts. It finds particular application in conjunction with an improved combination needle holder and suture cutter medical instrument for use in closing an incision or wound, and will be described with particular reference thereto.

It is known to use separate needle driver and scissors instruments during a medical procedure to close an incision or wound. In particular, the needle driver is used to pass a needle and depending suture through incised tissue. Thereafter, the scissors are used to cut the suture after a finishing knot has been tied in the suture.

It is burdensome, time consuming, and overly-complicated to repeatedly alternate between two separate medical instruments when placing individual stitches. In the case where no medical assistant is available to hand the instruments to the surgeon (or other person performing the suturing procedure), the surgeon must repeatedly pick-up and put-down the instruments thus increasing the chance of dropping or placing an instrument outside a sterile field surrounding the incision or wound. These problems compound when numerous stitches are required to close a relatively large incision or wound.

U.S. Pat. No. 2,315,326, issued to Gmeiner, discloses a combination needle holder and scissors instrument 10 that allows a surgeon to suture an incision or wound with a single instrument. As shown in FIG. 1, the Gmeiner instrument includes a pair of hingedly connected jaws 12a, 12b each having end teeth 14a, 14b for gripping a needle 16 (shown in cross-section) and a guide or stop block 18 therefore, together with a pair of longitudinally positioned shearing blades 20a, 20b between the stop block 18 and jaw pivot 22. The shearing blades 20a, 20b cooperate to shear or otherwise cut the suture in a scissors-like manner. The Gmeiner instrument also includes a pair of arms or handles 24a, 24b that have finger loops 26a, 26b and a lock mechanism 28a, 28b.

In operation, the jaws 12a, 12b of the Gmeiner instrument are clamped around a needle by bringing the loops 26a, 26b and depending handles 24a, 24b together to actuate the lock mechanism 28a, 28b in a known manner. Thereafter, the Gmeiner instrument is manipulated to pass the clamped needle and depending suture through the tissue. After a finishing knot has been placed in the suture, the jaws 12a, 12b of the Gmeiner instrument are unclamped from around the needle by deactuating the lock mechanism 28a, 28b to separate the handles 24a, 24b in a conventional manner. With the jaws (and handles) of the Gmeiner instrument open, the shearing blades 20a, 20b are positioned proximate the finishing knot and then actuated by bringing the handles 24a, 24b together to cut the suture in a scissors-like manner. It should be appreciated that the lock mechanism may be inadvertently actuated when bringing the handles together to sever the suture.

Thus, a disadvantage associated with the Gmeiner instrument is that the jaws must close in order to effectuate the scissors-like cutting of the suture. This not only involves properly positioning the shearing blades close to the finishing knot, but it also involves separately manipulating (i.e. closing the handles) the instrument to effectuate the cutting action. Two specific problems arise from this operation. First, as mentioned, the lock mechanism may be inadvertently actuated while cutting the suture. This locks the handles together, thus requiring the instrument to be unlocked before it can be used again to reclamp the same needle and remaining suture, or to clamp to a new needle and suture. The unlocking motion is an extra operation that disadvantageously increases the amount of time to complete the procedure and the amount of effort required to perform the procedure.

Second, the use of two shearing blades (or one die cut blade and a guide surface) requires relatively exact alignment of the instrument to the suture, i.e., perpendicular placement of the device relative to the finishing knot. Due to space constraints and/or the angle and area of the suture involved, this alignment may be difficult, thus hampering the cutting operation.

Accordingly, it has been considered desirable to develop a new and improved combination needle holder and suture cutter medical instrument for use in closing an incision or wound which meets the above-stated needs and overcomes the foregoing difficulties and others while providing better and more advantageous results.

SUMMARY OF THE INVENTION

In accordance with one aspect of the present invention, a medical instrument is disclosed. The surgical instrument includes a first handle pivotally joined to a second handle to define opposing jaws at a distal end of the surgical instrument, each of the jaws including a distal clamping portion and a blade portion proximate the clamping portion and each of the blade portions having a recessed cutting edge so as to define an aperture between the blade portions in a closed position of the surgical instrument, the distal clamping portions cooperating to clamp a needle and each of the recessed cutting edges adapted to independently sever a suture.

In accordance with another aspect of the present invention, a medical instrument is disclosed. The medical instrument includes a first handle pivotally joined to a second handle to define opposing jaws at a distal end of the medical instrument, each of the jaws including a distal clamping portion and at least one of the jaws including a blade portion proximate the respective clamping portion, the blade portion having a recessed cutting edge so as to define an aperture between the jaws in a closed position of the medical instrument, the distal clamping portions cooperating to clamp a needle and the recessed cutting edge adapted to independently sever a suture.

One advantage of the present invention is the provision of a combination needle holder and suture cutter medical instrument having at least one razor cutting edge portion that can be used to independently sever a suture without having to close the handles of the instrument.

Another advantage of the present invention is the provision of a combination needle holder and suture cutter medical instrument having at least one razor cutting edge portion that can be used to sever a suture with a simple swiping motion.

Yet another advantage of the present invention is the provision of a combination medical instrument that is used to place a suture and trim a finishing knot.

Still further advantages of the present invention will become apparent to those of ordinary skill in the art upon reading and understanding the following detailed description of the preferred embodiments.

BRIEF DESCRIPTION OF THE DRAWINGS

The invention may take form in various components and arrangements of components, and in various steps and arrangements of steps. The drawings are only for purposes of illustrating a preferred embodiment(s) and are not to be construed as limiting the invention.

FIG. 2 is a plan view of a combination needle holder and suture cutter medical instrument that incorporates the features of the present invention therein;

FIG. 3 is an enlarged cross-section view of the combination needle holder and suture cutter medical instrument taken along the line 3—3 in FIG. 2;

FIG. 4 is an alternate cross-section of the combination needle holder and suture cutter medical instrument taken along the line 4—4 in FIG. 2.

DETAILED DESCRIPTION OF THE INVENTION

Figure 1:
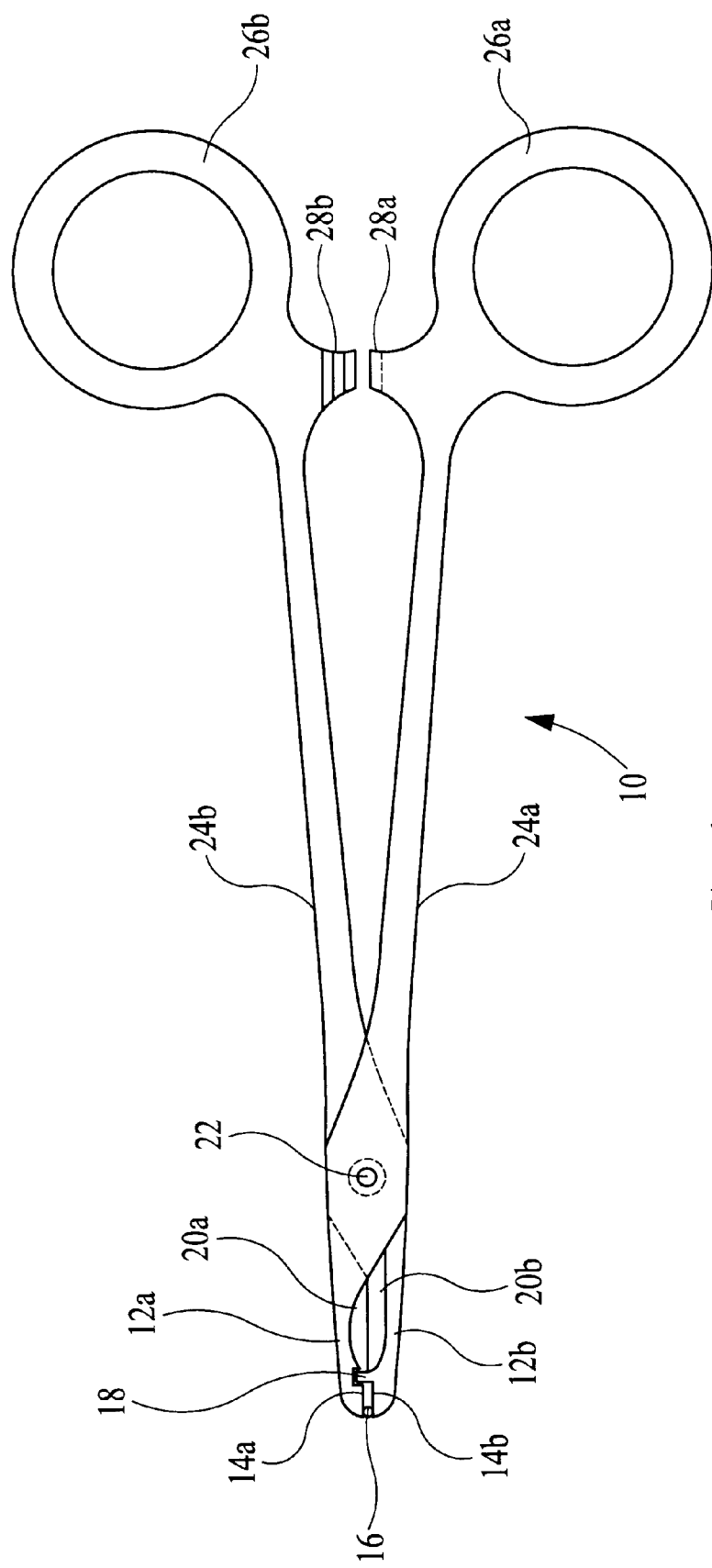
FIG. 1 is plan view of a known combination needle holder and scissors medical instrument.

With reference to FIG. 2, there is shown a combination needle holder and suture cutter medical instrument 100 that incorporates the features of the present invention therein. The instrument 100 includes a first arm 102a and a second arm 102b that are pivotally joined together by a conventional pivot means 104 such as a pin, screw, rivet, etc.

The first arm 102a includes a jaw portion 106a extending distally from the pivot 104 and an elongate handle portion 108a extending proximally from the pivot 14. Likewise, the second arm 102b includes a jaw portion 106b extending distally from the pivot 104 and an elongate handle portion 108b extending proximally from the pivot 104.

Each of the jaw portions 106a, 106b includes a distal clamping portion 110a, 110b and an intermediate blade portion 112a, 112b proximate the clamping portion 110a, 110b. The clamping portions 110a, 110b and blade portions 112a, 112b are formed integrally with the respective jaw portions 106a, 106b. The handle portions 108a, 108b each include a proximal finger loop portion 114a, 114b and a toothed lock member 116a, 116b. When actuated, the toothed lock members 116a, 116b cooperate in a known interlocking manner to hold the handles together. The clamping portions 110a, 110b each include a needle gripping surface that can be smooth, toothed, knurled, and/or textured to facilitate positively gripping a needle.

With continuing reference to FIG. 2, and particular reference to FIG. 3, each blade portion 112a, 112b includes a first (e.g. upper) surface 118a, 118b and a second (e.g. lower) surface 120a, 120b. Further, the blade portions 112a, 112b are each shaped so as to define an arcuate, or otherwise recessed, razor cutting edge 122a, 122b. That is, with the handles 108a, 108b in a closed and/or locked position, a gap or aperture 124 is defined between the blade portions 112a, 112b.

As shown in FIG. 3, the razor cutting edges 122a, 122b are positioned intermediate between the first and second surfaces 118, 120 of each blade portion 112a, 112b. Alternatively, as shown in FIG. 4, the razor cutting edge 122a, 122b can be formed integral with one of the surfaces such as the second cutting surface 120a, 120b. The combination needle holder and suture cutter medical instrument 100 can be formed from any known medical grade alloy materials, such as stainless steel, etc.

Figure 5:
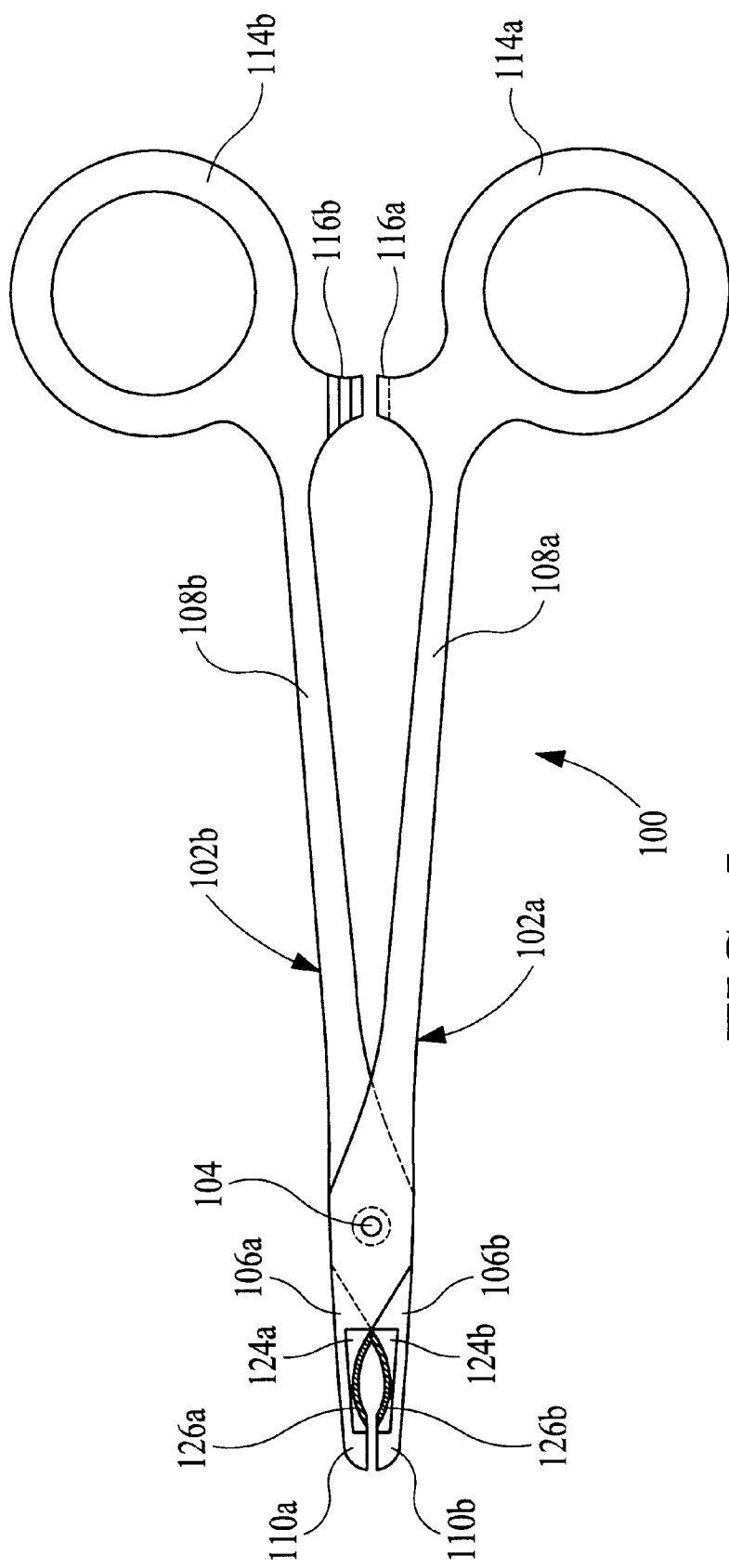
FIG. 5 is a plan view of another combination needle holder and suture cutter medical instrument that incorporates the features of the present invention therein.

With reference to FIG. 5, blade inserts 124a, 124b can be substituted for the integral blade portions 112a, 112b (FIGS. 2–4). The blade inserts 124a, 124b each include an arcuate, or otherwise recessed, razor cutting edge 126a, 126b. The blade inserts 124a, 124b are formed from any known medical grade alloy materials, such as stainless steel, etc. The remaining portion of the combination needle holder and suture cutter instrument of FIG. 5 (i.e. the arms 102a, 102b and depending structures), can be formed from medical grade materials other than stainless steel, such as plastic, polymeric, composite, glass, etc. Thus, the combination needle holder and suture cutter instrument of FIG. 5 can be produced as a single-use or disposable medical instrument.

In the case where the medical instrument is not disposable, the blade inserts 124a, 124b can be permanently or removably attached to the respective jaw portions 106a, 106b by any known attachment means such as adhesive bonding, chemical bonding, over-molding, and/or mechanical fasteners such as nuts, screws, bolts, etc. Removable blade inserts 124a, 124b can be designated as single-use (disposable) or multi-use (sterilizable).

In operation, the clamping portions 110a, 110b of the combination needle holder and suture cutter medical instrument of FIGS. 2–5 can be clamped around a needle by bringing the loops 114a, 114b and depending handles 108a, 108b together to actuate the lock mechanism 116a, 116b. Thereafter, the instrument 100 can be manipulated to pass the clamped needle and depending suture through the tissue. Either prior to, or after a finishing knot has been tied in the suture, the clamping portions 110a, 110b can be unclamped from around the needle by deactuating the lock mechanism 116a, 116b in order to separate or open the handles 114a, 114b.

With the jaws (and handles) of the instrument 100 remaining in an open position, either one of the blade portions 112a, 112b (depending on the preference of the user) can be positioned proximate the finishing knot. Thereafter, the suture can be severed by performing a simple swiping motion with the respective razor cutting edge 122a, 122b. After the suture has been severed, the clamping portions 110a, 110b can then be clamped around the same, or a new, needle by bringing the loops 114a, 114b and depending handles 108a, 108b together again to actuate the lock mechanism 116a, 116b.

It should be appreciated that the suture can be severed without the extra step of bringing the handles 108a, 108b together to actuate a scissors-like cutting motion, and without inadvertently actuating the locking mechanism 116a, 116b.

By recessing the razor cutting edges 122a, 122b, 126a, 126b, it is easier to position the suture within a blade portion, and easier to retain the suture within the blade portion when being severed. Further, by recessing the razor cutting edges 122a, 122b, 126a, 126b to provide the aperture 124, the surgeon's field of view is improved, thus making it easier to properly and accurately position one of the razor cutting edges with respect to the suture finishing knot. Moreover, since each of the blade portions are used independently, there is no need to align both blade portions with respect to the suture as required with the scissors and die-cutting instruments of the prior art.

The invention has been described with reference to the preferred embodiments. Obviously, modifications and alterations will occur to others upon reading and understanding the preceding detailed description. It is intended that the invention be construed as including all such modifications and alterations insofar as they come within the scope of the appended claims or the equivalents thereof.

For instance, in the embodiments of FIGS. 2–5, two blade portions 106a, 106b, 124a, 124b are illustrated. However, since each blade portion can be used independently to sever the suture, it is contemplated that one of the blade portions can be eliminated without departing from the scope of the present invention. Further, it is contemplated that the instrument of the present invention can incorporate a first guide or stop block 18 (FIG. 1) between the needle gripping portions 110 and the blade portions 112 and/or a guide or stop block between the blade portions 112 and the pivot 104.

What is claimed is:

1. A medical instrument comprising a first handle pivotally joined to a second handle to define opposing jaws at a distal end of the medical instrument, each of the jaws including a distal clamping portion and a blade portion proximate the clamping portion and each of the blade portions having a recessed cutting edge so as to define an aperture between the blade portions in a closed position of the medical instrument, the distal clamping portions cooperating to clamp a needle and each of the recessed cutting edges adapted to independently sever a suture.

2. The medical instrument of claim 1, wherein the medical instrument is a single-use instrument.

3. The medical instrument of claim 1, wherein the blade portions are attached to the jaws by attachment means.

4. The medical instrument of claim 1, wherein the blade portions are formed from a first material and the first and second handles are formed from a second material different than the first material.

5. The medical instrument of claim 1, wherein the first and second handles define opposing finger loops at a proximal end of the medical instrument.

6. The medical instrument of claim 5, wherein the first and second handles define opposing locking mechanisms at an intermediate portion of the medical instrument.

7. The medical instrument of claim 1, wherein the medical instrument is formed from a sterilizable material.

8. The medical instrument of claim 1, wherein the clamping portions each include a needle gripping surface.

9. The medical instrument of claim 1, wherein one of the recessed cutting edges is adapted to sever the suture with a swiping motion.

10. The medical instrument of claim 1, wherein one of the recessed cutting edges is adapted to sever the suture without closing the first and second handles.

11. A medical instrument comprising a first handle pivotally joined to a second handle to define opposing jaws at a distal end of the medical instrument, each of the jaws including a distal clamping portion and at least one of the jaws including a blade portion proximate the respective clamping portion, the blade portion having a recessed cutting edge so as to define an aperture between the jaws in a closed position of the medical instrument, the distal clamping portions cooperating to clamp a needle and the recessed cutting edge adapted to independently sever a suture.

12. The medical instrument of claim 11, wherein the medical instrument is a single-use instrument.

13. The medical instrument of claim 11, wherein the blade portion is attached to the respective jaw by an attachment means.

14. The medical instrument of claim 11, wherein the blade portion is formed from a first material and the first and second handles are formed from a second material different than the first material.

15. The medical instrument of claim 11, wherein the first and second handles define opposing finger loops at a proximal end of the medical instrument.

16. The medical instrument of claim 15, wherein the first and second handles define opposing locking mechanisms at an intermediate portion of the medical instrument.

17. The medical instrument of claim 11, wherein the medical instrument is formed from a sterilizable material.

18. The medical instrument of claim 11, wherein the clamping portions each include a needle gripping surface.

19. The medical instrument of claim 11, wherein the recessed cutting edge is adapted to sever the suture with a swiping motion.

20. The medical instrument of claim 11, wherein the recessed cutting edge is adapted to sever the suture without closing the first and second handles.

* * * * *